United States Patent
Rogers et al.

(10) Patent No.: US 6,831,738 B2
(45) Date of Patent: Dec. 14, 2004

(54) METHOD AND APPARATUS FOR INSPECTING END SURFACES ON OPTICAL CONNECTORS

(75) Inventors: Charles J. Rogers, Mounds View, MN (US); Marlon E. Holmquist, Gibbon, MN (US)

(73) Assignee: ADC Telecommunications, Inc., Eden Prairie, MN (US)

( * ) Notice: Subject to any disclaimer, the term of this patent is extended or adjusted under 35 U.S.C. 154(b) by 256 days.

(21) Appl. No.: 09/892,192

(22) Filed: Jun. 26, 2001

(65) Prior Publication Data

US 2002/0197052 A1 Dec. 26, 2002

(51) Int. Cl.$^7$ .......................... G01N 21/01; G02B 6/00
(52) U.S. Cl. .................. 356/244; 356/73.1; 385/147
(58) Field of Search .............................. 356/244, 73.1, 356/72–73, 450, 511; 324/72.5, 538, 754, 761; 385/53, 60, 78, 147

(56) References Cited

U.S. PATENT DOCUMENTS

| | | | | |
|---|---|---|---|---|
| 4,933,816 A | * | 6/1990 | Hug et al. ................. 362/551 |
| 5,455,515 A | * | 10/1995 | Saijo et al. ................. 324/538 |
| 5,459,564 A | | 10/1995 | Chivers | |
| 5,467,023 A | * | 11/1995 | Takeyama ................. 324/754 |
| 5,724,127 A | | 3/1998 | Csipkes et al. | |
| 5,731,893 A | | 3/1998 | Dominique | |
| 5,883,995 A | | 3/1999 | Lu | |
| 6,142,676 A | | 11/2000 | Lu | |
| 6,215,555 B1 | | 4/2001 | Chivers | |

FOREIGN PATENT DOCUMENTS

| | | | | |
|---|---|---|---|---|
| JP | 05118831 A | * | 5/1993 | ........... G01B/11/24 |
| JP | 0485629 B1 | * | 2/1995 | |
| JP | 08278108 A | * | 10/1996 | ........... G01B/11/00 |
| JP | 11002738 A | * | 1/1999 | ........... G02B/6/24 |
| JP | 11-132717 | | 5/1999 | |
| JP | 2000-214350 | | 8/2000 | |

* cited by examiner

Primary Examiner—Frank G. Font
Assistant Examiner—Sang H. Nguyen
(74) Attorney, Agent, or Firm—Merchant & Gould P.C.

(57) ABSTRACT

Methods and apparatus fix relative rotation between an optical connector about an axis that runs longitudinally through the optical connector and an inspection machine. In one method, an optical connector is releasably secured to a cage member having an extending flange. The optical connector is mounted into an inspection machine by inserting the end surface of the connector into a connector receipt aperture of the machine, and orienting the optical connector with the cage member to position the extending flange within a void of a fixture on the machine. A kit including a cage member and a mounting plate are provided.

15 Claims, 6 Drawing Sheets

METHOD AND APPARATUS FOR INSPECTING END SURFACES ON OPTICAL CONNECTORS

TECHNICAL FIELD

This disclosure concerns a method and apparatus for holding or inspecting an end surface of an optical connector, wherein the connector includes a housing holding an optical ferrule with an optical fiber. In particular, this disclosure addresses a method and apparatus for fixing relative rotation between an optical connector and an inspection machine.

BACKGROUND OF THE INVENTION

Optical connectors, including a housing holding the optical ferrule with an optical fiber, have end faces or surfaces that need to be a certain, optimum shape to prevent misalignments, air gaps, reflections, or scattering of light at interfaces at which optical fibers need to be coupled in an optical fiber link. Because of the precision needed, the end faces of optical connectors need to be inspected. Imperfections in the end faces of optical connectors are compounded by being summed with similar imperfections at other fiber junctions in the system and ultimately can lead to greatly increased light attenuation, lower signal to noise ratios, and lower system band width.

In some systems, to help preserve band width, connectors have been developed with angled cuts. In these types of arrangements, the ferrule is angle ground and then polished. Such angled polished connectors help to reduce incidents of back reflection. Back reflection is caused by two mating fiber ends that do not achieve physical contact with each other, creating a small air gap in the transmission path of the signal, which leads to back reflection of the laser light from the unmatched interface. To assure the necessary physical contact between two mating fibers, the ends can be angled and polished, as described above, and factors such as radius of curvature, fiber height, and apex offset of the polish with respect to the center of the fiber is controlled. These types of parameters will help to insure physical contact between the fibers, thereby minimizing loss and back reflection.

Before these connectors are installed in the field, they need to be inspected to measure, for example, the radius of curvature, the apex offset, and the fiber height. Various inspection machines have been developed for providing this type of testing. In general, these machines utilize interferometer based systems. One machine is commercially available from Direct Optical Research Company (DORC) of Phoenix, Ariz. The DORC machine uses an interferometer with a parfocal, parcentral zoom lens to inspect and measure an end surface of an optical fiber connector. DORC machines support the connector on a stage that is movable about three axes (X, Y, and Z axes) and the interferometer is set to a microscope mode. Controls of the stage along the X, Y, and Z axes are adjusted to bring the end surface into focus and alignment with the optical axis of the interferometer. The DORC machine also has a tilt stage that can be oriented to facilitate measurement of an angle on the end surface or protrusion or undercut of fiber with respect to the ferrule of a connector without readjusting the main stage. Further details about the DORC machine are described in U.S. Pat. No. 5,459,564 issued Oct. 17, 1995, and U.S. Pat. No. 6,215,555 issued Apr. 10, 2001, each of which is incorporated by reference herein.

Improvements in methods and apparatus for inspecting connector ends are desirable.

SUMMARY OF THE DISCLOSURE

In general, methods and apparatus are provided for improving ways to hold or inspect an end surface of an optical connector. In particular, methods and apparatus are provided to fix relative rotation between an optical connector (about an axis that runs longitudinally through the optical connector) and an inspection machine.

In one method, in accordance with principles of the invention, an inspection machine is provided that includes a connector receipt aperture and a fixture defining a void. The optical connector is releasably secured to a cage member. The cage member preferably includes an extending flange. The optical connector is mounted into the inspection machine by inserting the end surface of the connector into the connector receipt aperture of the machine, and orienting the optical connector with the cage member to position the extending flange within the void of the fixture.

Also in accordance with principles of the invention, a cage member for an optical connector is disclosed. The cage member is provided for holding or fixing the relative rotation between the optical connector and an inspection machine. Preferably, the cage member comprises a frame defining an optical connector receiving chamber and having a longitudinal axis. The cage member also preferably includes a latch assembly that extends from the frame and is positioned adjacent to the receiving chamber. Further, the cage member preferably includes a flange that is cantilevered from the frame and oriented generally normal to the longitudinal axis. The flange will be arranged to be long enough such that it extends and fits into a receiving void fixed on the inspection machine.

Also, in accordance with principles of this disclosure, a mounting plate is provided.

Further, in accordance with principles of this disclosure, a combination of an optical connector and a cage member are provided.

In another aspect, this disclosure provides a kit for use with an inspection machine for inspecting an end surface of an optical connector. The kit includes a plate and a cage member. Preferably, the plate is constructed and arranged to be mounted on the inspection machine. The plate has an edge that defines a receiving void. The cage member is constructed and arranged to receive an optical connector. The cage member preferably includes an extending flange. The extending flange is sized to project into and be received by the receiving void of the plate.

Further, in accordance with principles of this disclosure, a mounting arrangement for use with an inspection machine for inspecting an end surface of an optical connector includes a cradle; a jig supported by the cradle; a chuck within the jig; a fixture mounted on the jig; the fixture defining a receiving void; and an optical connector mounted in a cage member. The optical connector includes a housing holding an optical ferrule with an optical fiber. The optical connector is mounted within, and held by, the chuck. The cage member includes an extending flange, and the extending flange is received within the receiving void of the fixture.

DETAILED DESCRIPTION OF THE PREFERRED EMBODIMENT

A. Some Problems with Existing Inspection Machines

The term "clocking" refers to the rotational or angular position of an optical connector relative to an inspection machine. In particular, an optical connector defines a longitudinal axis therethrough. The optical connector may be rotated about that longitudinal axis before positioning the connector into a jig of an inspection machine. Current inspection machines, such as the DORC machine described in U.S. Pat. No. 5,459,564, do not allow for accurate clocking of the optical connector relative to the inspection machine. Because of the geometry of the end face that is being measured, the measurement is extremely sensitive to clocking. Thus, there is a need to provide methods and apparatus to allow for accurate fixing of the rotational or angular position of the optical connector relative to the inspection machine.

B. The Embodiment of FIGS. 1–8

Figure 1:
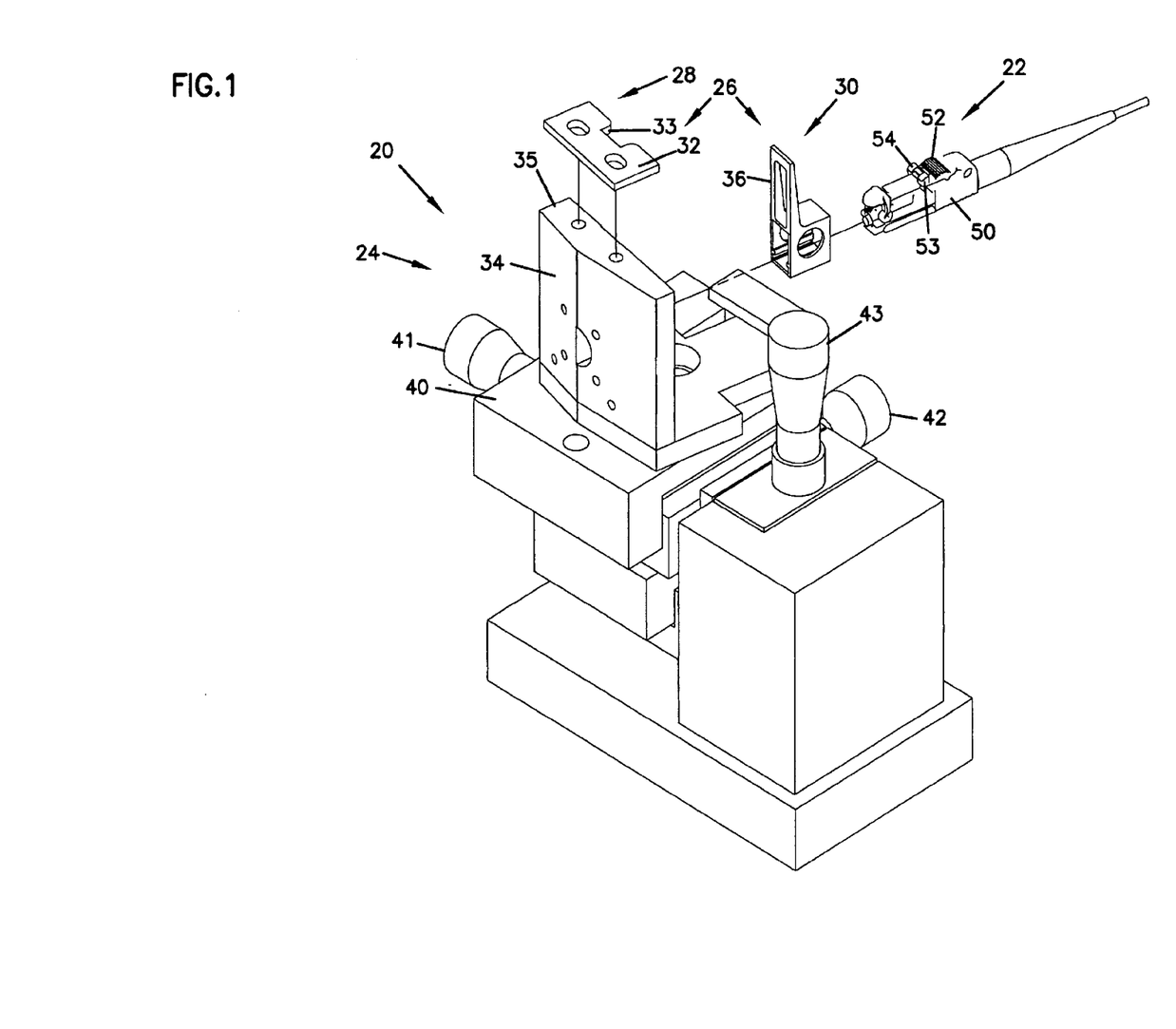
FIG. 1 is an exploded, perspective view of one embodiment of a portion of an inspection machine adapted with a cage and a fixture, constructed according to principles of this disclosure.

FIG. 1 illustrates a portion of an inspection machine 20. The inspection machine is a type of inspection and testing machine designed to measure end faces of optical fiber connectors that include a housing holding an optical ferrule with an optical fiber. Such machines are available from Direct Optical Research Company of Phoenix, Ariz. In general, the inspection machine 20 includes an interferometer and will measure radius, apex offset, fiber height, angle, and surface roughness. The machine will produce a topographical map of the end surface of optical connectors. One usable machine, available from DORC, is the machine described in U.S. Pat. Nos. 5,459,564 and 6,215,555, each of which is incorporated herein by reference.

The portion of the inspection machine 20 that is shown in FIG. 1 is generally the portion that holds and positions an optical connector 22 relative to an interferometer (not shown). FIG. 1 is a partially exploded, perspective view. In FIG. 1, the pre-existing, DORC machine is shown assembled at 24, and a kit 26 to fit to the machine 24 in order to provide for accurate clocking of the optical connector 22 relative to the machine 24 is shown exploded from the machine 24.

In general, the kit 26 includes a fixture 28 and a cage member 30. The fixture 28, as embodied herein, is a plate 32 constructed and arranged to be mounted on the machine 24. In particular, the machine 24 includes a jig 34 for holding the optical connector 22. The jig 34 has a top surface 35, which receives the plate 32. Further details about the plate 32 are described below.

In general, the cage member 30 is constructed and arranged to receive the optical connector 22. In preferred embodiments, the cage member 30 includes an extending flange 36. The extending flange 36 is sized to project into and be received by void 33 in the plate 32. The flange 36 received within the void 33 is viewable in FIG. 2. The flange 36 being trapped within the void 33 provides for a fixed angled position of the optical connector 22 relative to the inspection machine 24.

Many different types of optical connectors 22 are usable with the cage member 30 and fixture 28. The particular optical connector 22 illustrated in the drawings is an LX.5, commercially available from ADC Telecommunications of Minnetonka, Minn., the assignee of this patent. The LX.5 connector is described in detail in U.S. Pat. Nos. 6,142,676 and 5,883,995, each of which is incorporated herein by reference.

Figure 2:
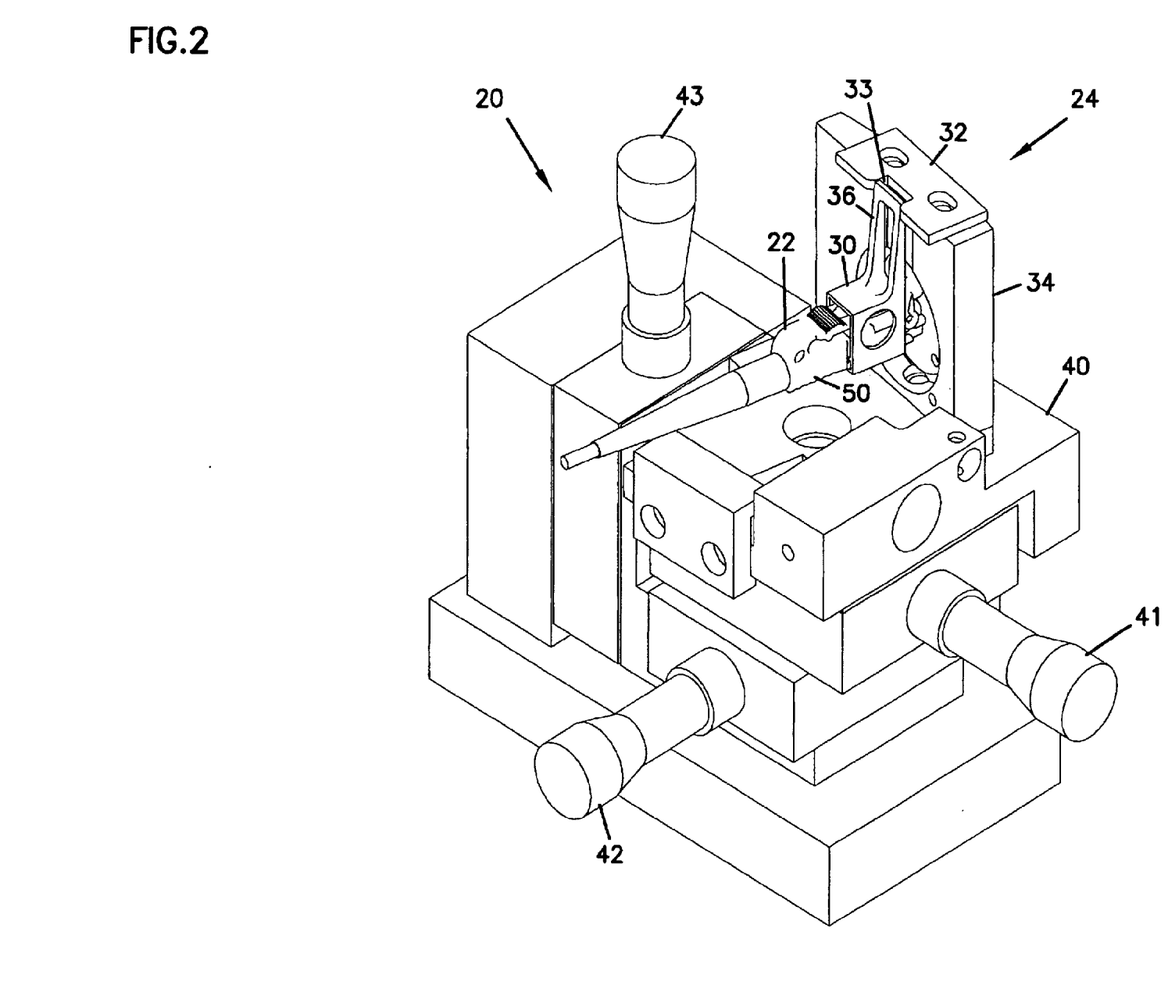
FIG. 2 is a perspective view of the inspection machine, assembled, depicted in FIG. 1.

FIG. 2 shows the optical connector 22 positioned within the cage member 30, with the connector end 38 (FIG. 4) being positioned within and held by the inspection machine 24. Also note at FIG. 2 that the extending flange 36 is nestled within the void 33 of the plate 32. The inspection machine 24 includes a stage or a cradle 40 that is adjustable in the X, Y and Z axes by way of adjustment knobs 41, 42, and 43. These adjustments will move the jig 34 to help orient the connector end 38 for proper inspection. The jig 34 is also rotatable in a plane parallel to the cradle 40 and the top surface 35 (FIG. 1) of the jig 34.

Figure 3:
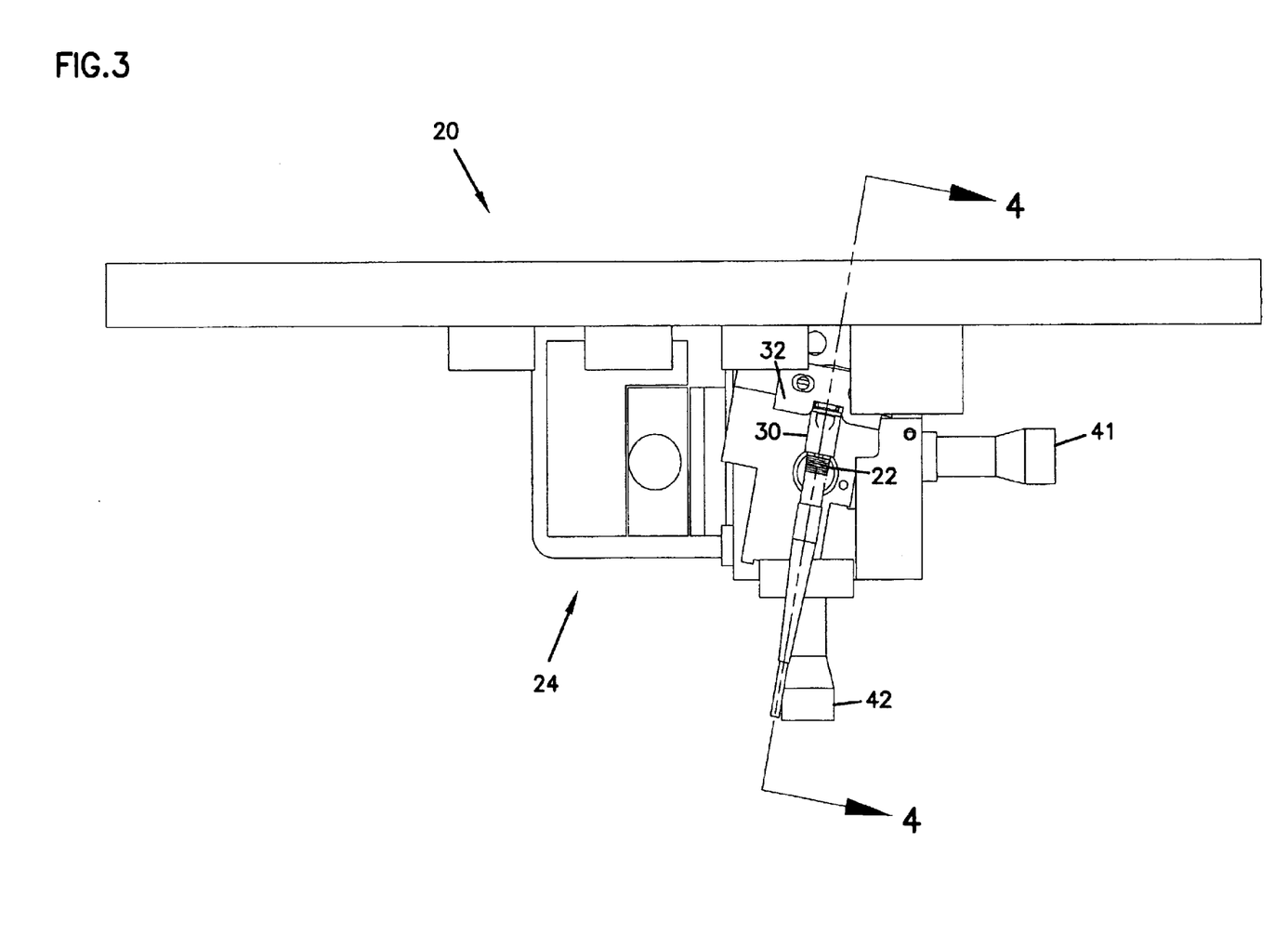
FIG. 3 is a plan view of the inspection machine depicted in FIG. 2.
Figure 4:
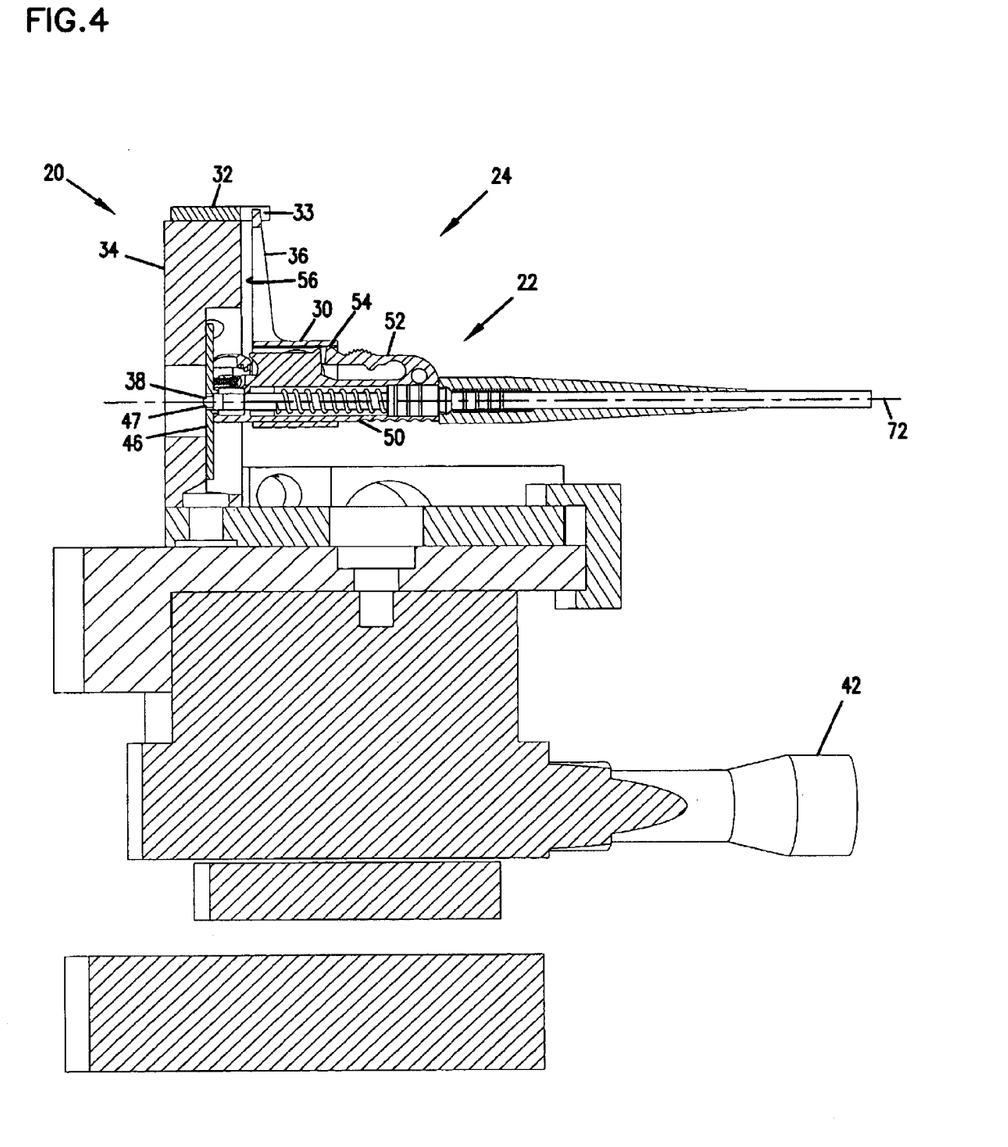
FIG. 4 is a schematic, cross-sectional view of the inspection machine shown in FIG. 3, the cross-section being taken along the line 4—4 of FIG. 3.

In FIG. 3, a plan view of the connector 22 mounted within the inspection machine 24 is shown. A schematic, cross-sectional view along the line 4—4 of FIG. 3 is shown in FIG. 4. In FIG. 4, the optical connector 22 secured by a chuck 46 within the jig 34 can be seen. The chuck 46 defines a connector receipt aperture 47 that receives the connector 22. The connector end 38, comprising a ferrule holding an optical fiber is positioned within the aperture 47. The cage member 30 is secured to the optical connector 22 by way of latching. The connector 22 illustrated includes a housing 50 and a clip 52. The clip 52 includes a pair of hooks 53, 54 (FIG. 1) that are used to engage and mateably connect with the cage member 30.

Still in reference to FIG. 4, note that the cage member 30, including the flange 36, forms a flat, planar surface 56 that is spaced from the jig 34. The connector 22 extends through the cage member 30 and protrudes from and projects out of the flat face 56.

Figure 5:
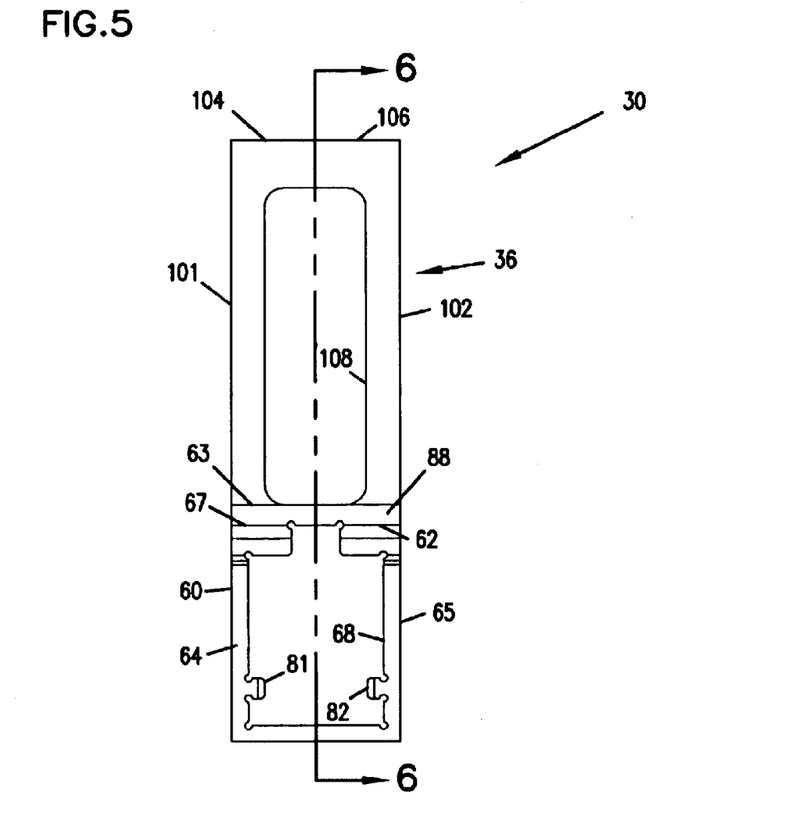
FIG. 5 is a front elevational view of an embodiment of a cage member adapted for use of the inspection machine depicted in FIGS. 1–4, constructed according to principles of this disclosure.
Figure 6:
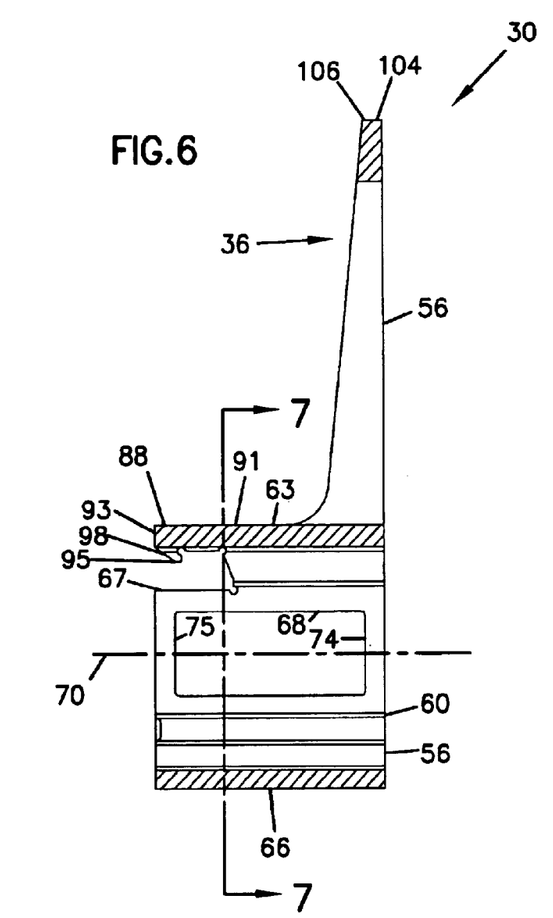
FIG. 6 is a cross-sectional view of the cage member shown in FIG. 5, the cross-section being taken along the line 6—6 of FIG. 5.
Figure 7:
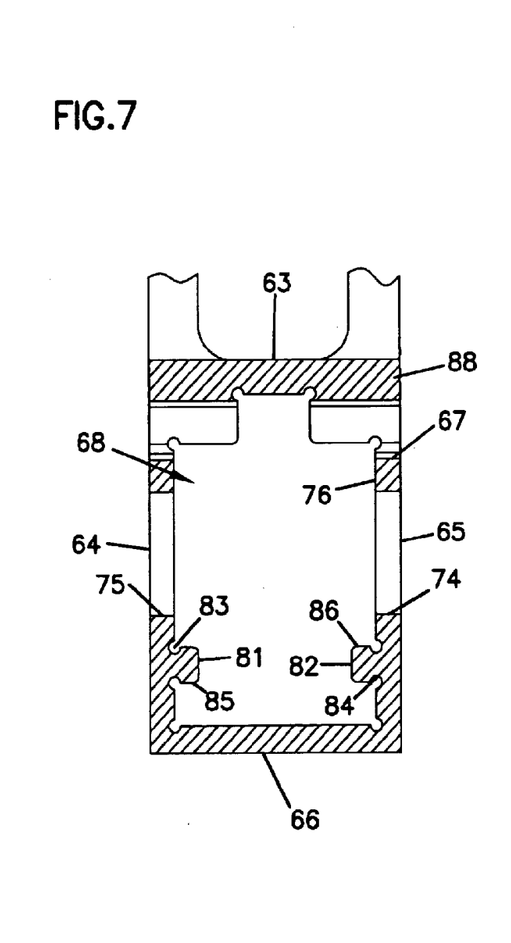
FIG. 7 is an enlarged, fragmented, cross-sectional view of a portion of the cage member; the cross-section being taken along the line 7—7 of FIG. 6.

Attention is now directed to FIGS. 5–7, where the cage member 30 is illustrated in detail. The cage member 30 includes a frame 60, a latch assembly 62, and the extending flange 36. The frame 60 has a frame top 63 and an adjacent generally rectangular, receiving chamber 68. The receiving chamber 68 has first and second chamber sides 64, 65, a bottom 66 and a top 67. The frame 60, including sides 64, 65, bottom 66 and chamber top 67 together define the receiving chamber 68 in an interior volume. The receiving chamber 68 is sized to receive optical connector 22 therein. The receiving chamber 68 defines a longitudinal axis 70, which is aligned with the longitudinal axis 72 (FIG. 4) of the connector 22. The frame 60 has a height that extends between bottom 66 and frame top 63. Of course, this height is sufficient to accommodate the receipt of the optical connector 22. As described below, this height is less than the height of the extending flange 36.

The chamber sides 64, 65 each define apertures 74, 75. Further, the chamber top 67 also has a void 76. These apertures 74, 75 and void 76 contribute to having an overall cage member 30 that has a mass light enough such that it does not interfere with accurate measurements by the inspection machine 24. Indeed, in preferred embodiments, where the cage member 30 is constructed out of a strong, durable material such as hardened tool steel (440 C stainless steel, full hard), the cage member 30 has a weight of under 3 grams. The hardened tool steel also results in a cage member 30 that is resistant to abrasion.

Extending or projecting from the frame 60 are first and second ribs 81, 82. In particular, the first rib 81 extends from and is cantilevered from side 64 to project into the receiving chamber 68. Analogously, the second rib 82 extends from and is cantilevered from the side 65 to project into the receiving chamber 68. Note that each rib 81, 82 has a cross-section including a stem 83, 84 leading to a generally rectangular-shaped head 85, 86. Each of the heads 85, 86 has an overall width that is greater than the width across each of the stems 83, 84. The ribs 81, 82 help to orient and align the optical connector 22 within the receiving chamber 68. Each of the ribs 81, 82 generally extends the entire length of each respective side 64, 65. The ribs 81, 82 extend in the direction that is parallel to the longitudinal axis 70.

One of the features of the cage member 30, and the shape of the receiving chamber 68 in particular, is that once the connector 22 is installed within the receiving chamber 68, the connector 22 is allowed to relax to its own natural state. This leads to more accurate measurements by the testing machine 24.

In reference now in particular to FIGS. 5 and 6, the latch assembly 62 can be seen as extending from the frame 60 in a direction generally parallel to the longitudinal axis 70. In the particular embodiment illustrated, the latch assembly 62 includes a latch member 88 having an extension 91 projecting from the frame 60 in a direction generally parallel to the longitudinal axis 70. Extension 91 has a free end 93 that terminates with a hook construction 95. The latch member 88 is rigid and not deflectable along its extension 91. The hook construction 95 is oriented to engage the hooks 53, 54 on the connector 22. The hook construction 95 includes a beveled surface 98 (FIG. 6) to allow for the latch member 88 to cam against the mating hooks 53, 54 and snap into engagement.

In reference now to FIG. 5, in the particular embodiment depicted, the extending flange 36 includes a pair of substantially parallel sides 101, 102. In preferred embodiments, the sides 101, 102 are parallel but may have a slight angle toward each other, such as less than 0.2 degrees. Each of the sides 101, 102 terminate at a free end 104. The free end 104 defines a top side 106. The width of the top side 106 is related to the width of the void 33, such that there is a precise fit. More details on the relationship between the width of the top side 106 and the width of the void 33 are described below.

The flange 36 has a height that extends from the top of the frame 63 to the top side 106. This height is sufficiently long to permit the connector 22 to be installed within the jig 34 and project into the void 33 in the fixture 28. In typical embodiments, the height of this flange 36 is at least 25% more than the height of the frame 60. In many embodiments, the height of the flange 36 is at least 50% more than the height of the frame 60.

In FIG. 5, it can be seen that the flange 36 defines an aperture 108. This aperture 108 contributes to the cage member 30 as having a very small mass, as discussed above.

Figure 8:
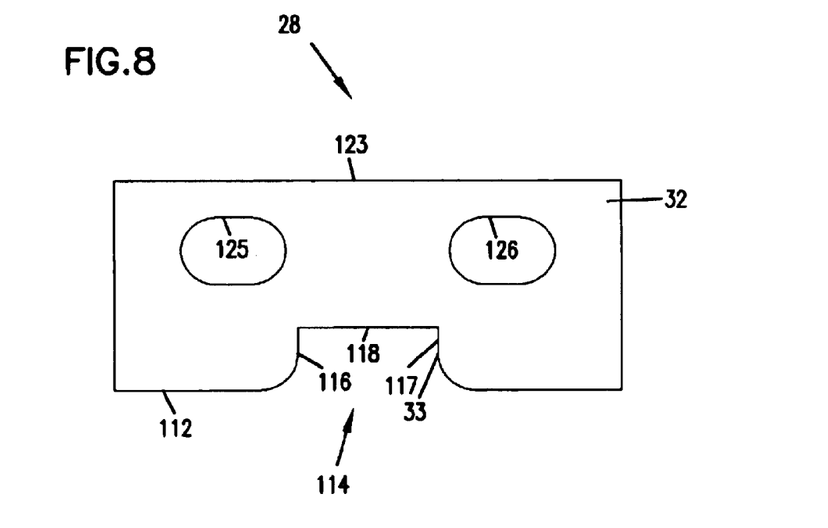
FIG. 8 is a plan view of one embodiment of a fixture utilized with the inspection machine depicted in FIGS. 1–4, constructed according to principles of this disclosure.

In reference now to FIG. 8, a plan view of the fixture 28 is illustrated. The plate 32 includes an edge 112, which defines the void 33. The void 33, as described above, is sized to receive the flange 36. The receiving void 33 generally comprises an open slot 114 having first and second sides 116, 117 and an end edge 118. The end edge 118 extends between the first and second sides 116, 117. As can be seen in FIG. 8, the first and second sides 116, 117 are perpendicular to both the plate edge 112 and the end edge 118, in preferred embodiments. Thus, in preferred embodiments, the end edge 118 is generally parallel to the plate edge 112.

The slot 114 has a width that corresponds to the distance between the sides 116, 117. This width is related to the width across the flange 36. In preferred embodiments, these widths are precisely related. This is because if the width of the slot 114 is too much greater than the width across the flange 36, then there will not be fixing of the rotational angle of the connector 22 within the inspection machine 24. In other words, there would be too much "wiggle room" that the connector 22 could move about. In that case, clocking would not be controlled. Conversely, if the width of the slot 114 is smaller than the width of the flange 36, the flange 36 will not be able to be received within the slot 114. This would also prevent the fixing of the relative rotation between the connector 22 and the inspection machine 24.

In preferred embodiments, the width of the slot 114 is no more than 0.25% of the width of the flange 36. Indeed, in many preferred embodiments, the width of the slot 114 is no more than 0.2% and is often no more than 0.1% of the width across the flange 36. It has been found that, in general, these widths allow for the receipt of the flange 36 within the slot 114 and do not permit movement of the flange 36 between the sides 116, 117 of the slot 114. Thus, clocking of the connector 22 is controlled.

Other features of the plate 32 can be embodied in many forms. In the particular embodiment illustrated, the plate 32 is generally rectangular in shape, with parallel sides 121, 122 and side 123 being parallel to the edge 112. Sides 121, 122 extend between edge 112 and side 123.

The plate 32 is constructed and arranged to be removable and replaceable with respect to the inspection machine 24. Although the plate 32 is constructed of a strong, durable material, such as hardened tool steel (440 C stainless steel, full hard), it is anticipated that after continued use, the slot 114 may be worn, causing the width across the slot 114 to become larger than can be tolerated for accurate measurements. Thus, after a period of use, the plate 32 will be removed from the machine 24 and replaced with a new plate 32.

The plate 32 defines apertures 125, 126 to allow for the orientation of fasteners therewithin to permit secure attachment and removal of the plate 32 onto the jig top surface 35. Each of the apertures 125, 126 is elongated, to permit some adjustment of the plate 32 relative to the jig 34 when mounting.

In FIG. 4, a cross-section of the plate 32 is viewable. Note that the bottom surface of the plate 32 is a smooth, planar surface. In general, the plate 32 has a thickness of less than 1/10th of an inch.

In operation, to inspect the end surface 38 of the connector 22, the connector 22 is releasably secured to the cage member 30. This is done by inserting the connector 22 into the receiving chamber 68 of the cage member 30 and latching the cage member 30 to the connector 22 by engagement between the latch assembly 62 and the clip 52 on the connector 22. The connector 22 with the cage member 30 is then mounted into the inspection machine 24 by inserting the connector end 38 into the connector receipt aperture 47 in the chuck 46. The connector 22 with the cage member 30 secured thereto is then oriented to position the extending flange 36 into the slot 114 of the fixture 28. The inspection machine 24 is then operated to inspect the connector end 38.

After inspection is completed, the connector 22 is dismounted from the inspection machine 24. This is done by removing the connector end 38 from the connector receipt aperture 47 and removing the extending flange 36 from the slot 114. The cage member 30 may then be removed from the connector 22 by releasing the engagement between the latch assembly 62 and the clip 52.

The above specification, examples and data provide a complete description of the manufacture and use of the invention. Many embodiments of the invention can be made.

What is claimed is:

1. A method for inspecting an end surface of an optical connector, the method comprising:
   (a) providing an inspection machine having a connector receipt aperture and a fixture defining a slot; the slot having first and second sides and an end edge between the first and second sides;
   (b) releasably securing the optical connector to a cage member including an extending flange; the optical connector including a housing holding an optical ferrule with an optical fiber; and
   (c) mounting the optical connector with the cage member secured thereto into the inspection machine by:
      (i) orienting the optical connector with the cage member to position the extending flange within the slot between the first and second sides of the fixture, and inserting the end surface of the optical connector into the connector receipt aperture.

2. A method according to claim 1 wherein:
   (a) said step of providing an inspection machine includes providing an inspection machine with a fixture defining a slot having a first width; and
   (b) said step of releasably securing the optical connector to a cage member includes securing a cage member having an extending flange; the flange defining a second width;
      (i) the first width being no more than 0.25% larger than the second width.

3. A method according to claim 1 wherein:
   (a) said step of releasably securing the optical connector to a cage member includes securing the optical connector to a cage member having a frame and a latch arrangement extending from the frame;
      (i) the frame defining a receiving chamber having a longitudinal axis; and
      (ii) the extending flange being cantilevered from the frame and oriented generally normal to the longitudinal axis of the receiving chamber.

4. A method according to claim 3 wherein:
   (a) said step of releasably securing the optical connector to a cage member includes:
      (i) inserting the optical connector into the receiving chamber; and
      (ii) latching the cage member to the optical connector with the latch arrangement.

5. A method according to claim 4 wherein:
   (a) said step of inserting the optical connector into the receiving chamber includes aligning the optical connector with guiding ribs projecting from the frame into the receiving chamber.

6. A method according to claim 4 further including:
   (a) after said step of mounting the optical connector into the inspection machine, unmounting the optical connector from the inspection machine by:
      (i) removing the end surface of the optical connector from the connector receipt aperture; and
      (ii) removing the extending flange of the cage member from the fixture slot; and
   (b) after said step of unmounting the optical connector from the inspection machine, removing the cage member from the optical connector by releasing the latch arrangement from the optical connector.

7. A method according to claim 1 wherein:
   (a) said step of providing an inspection machine having a connector receipt aperture and a fixture defining a slot includes mounting the fixture with the slot onto the inspection machine.

8. A kit for use with an inspection machine for inspecting an end surface of an optical connector, the connector including a housing holding an optical ferrule with an optical fiber; the kit comprising:
   (a) a plate constructed and arranged to be mounted on the inspection machine; said plate having an edge;
      (i) said edge defining a receiving void;
      (ii) said receiving void comprising a slot having first and second sides and an end edge;
         (A) said first and second sides being perpendicular to said plate edge;
         (B) said end edge extending between said first and second side;
         (C) said end edge being spaced from said plate edge by at least 0.1 inch; and
   (b) a cage member constructed and arranged to receive the optical connector; said cage member including an extending flange;
      (i) said extending flange being sized to project into and be received by the receiving void of the plate.

9. A kit according to claim 8 wherein:
   (a) said plate includes a pair of apertures sized to receive fasteners of secure said plate to the inspection machine;
      (i) said slot being centered between said pair of apertures.

10. A kit according to claim 8 wherein:
    (a) said cage member includes a frame defining an optical connector receiving chamber having a longitudinal axis;
       (i) said flange being cantilevered from said frame and oriented generally normal to said longitudinal axis
    (b) a latch assembly; said latch assembly extending from said frame and positioned adjacent to said receiving chamber.

11. A kit according to claim 10 wherein:
    (a) said flange includes a pair of parallel sides terminating at a free end;
       (i) said flange parallel sides being received within said slot between said first and second sides of said slot.

12. A kit according to claim 11 wherein:
    (a) said slot has a first width extending between said slot first and second sides; and
    (b) said flanges has a second width, extending between said flange parallel sides;
       (i) the first width being no more than 0.25% of the second width.

13. A kit according to claim 10 wherein:
    (a) said latch assembly on said cage member extends from said frame in a direction generally parallel to said longitudinal axis; and said latch assembly includes first and second spaced latch members; each of the first and second latch members having an extension projecting from said frame having a hook construction; and
    (b) said cage member further includes first and second guide ribs projecting from said frame into said receiving chamber;

(i) said first and second guide ribs opposing each other within said receiving chamber.

14. A fixture for use with an inspection machine for inspecting an end surface of an optical connector, the connector including a housing holding an optical ferrule with an optical fiber; the fixture comprising:

(a) a plate; said plate including:
 (i) a flat, planar mounting surface;
 (ii) a front edge;
  (A) said edge defining a receiving void;
  (B) said receiving void including an open slot having first and second sides and an end edge;
   (1) said end edge extending between said first and second sides; said first and second sides being perpendicular to said end edge and said front edge; said end edge being parallel to said front edge; and
   (2) said end edge being spaced from said front edge by at least 0.1 inch.

15. A fixture according to claim 14 wherein:

(a) said plate further includes at least one mounting aperture extending therethrough.

* * * * *

UNITED STATES PATENT AND TRADEMARK OFFICE
CERTIFICATE OF CORRECTION

PATENT NO. : 6,831,738 B2
DATED : December 14, 2004
INVENTOR(S) : Rogers et al.

It is certified that error appears in the above-identified patent and that said Letters Patent is hereby corrected as shown below:

Column 8,
Line 24, delete "side" and insert -- sides --.

Signed and Sealed this

Fifth Day of April, 2005

JON W. DUDAS
*Director of the United States Patent and Trademark Office*